(12) United States Patent
Franke et al.

(10) Patent No.: US 10,065,895 B2
(45) Date of Patent: Sep. 4, 2018

(54) COLOURING SOLUTION FOR DENTAL CERAMIC ARTICLES AND RELATED METHODS

(75) Inventors: Ruediger Franke, Herrsching (DE);
Gallus Schechner, Seefeld (DE);
Holger Hauptmann, Sindelsdorf (DE);
Robert Schnagl, Jengen (DE)

(73) Assignee: 3M Innovative Properties Company, St. Paul, MN (US)

( * ) Notice: Subject to any disclaimer, the term of this patent is extended or adjusted under 35 U.S.C. 154(b) by 611 days.

(21) Appl. No.: 12/669,846

(22) PCT Filed: Jul. 10, 2008

(86) PCT No.: PCT/US2008/069595
§ 371 (c)(1),
(2), (4) Date: Jan. 20, 2010

(87) PCT Pub. No.: WO2009/014903
PCT Pub. Date: Jan. 29, 2009

(65) Prior Publication Data
US 2010/0221683 A1 Sep. 2, 2010

(30) Foreign Application Priority Data

Jul. 23, 2007 (EP) .................................... 07112920

(51) Int. Cl.
*A61C 19/06* (2006.01)
*C09K 3/00* (2006.01)
(Continued)

(52) U.S. Cl.
CPC ........ *C04B 41/5007* (2013.01); *A61K 6/0002* (2013.01); *C04B 41/009* (2013.01);
(Continued)

(58) Field of Classification Search
CPC .............. C04B 41/009; C04B 41/5007; C04B 2103/0021; C04B 2103/0025;
(Continued)

(56) References Cited

U.S. PATENT DOCUMENTS 1,447,276 A 3/1923 Binder
2,807,555 A 9/1957 Short et al.
(Continued)

FOREIGN PATENT DOCUMENTS

AU 200026701 B2 * 8/2000 ............. C04B 41/82
DE 2012304 9/1971
(Continued)

OTHER PUBLICATIONS

CRC Handbook of Chemistry and Physics, 76th Edition, 1995-1996, CRC Press, Boca Raton, 12-14-12-15.
(Continued)

*Primary Examiner* — Shuangyi Abu Ali

(57) ABSTRACT

The invention relates to a coloring solution for coloring a dental ceramic article, the solution comprising: a solvent and a coloring agent, comprising rare earth element metals or ions being present in the solution in an amount of at least about 0.05 mol/l solvent and transition metals or ions being present in the solution in an amount of about 0.00001 to about 0.05 mol/l solvent. The invention also relates to a process for coloring dental ceramic articles, dental ceramic articles treated either with the coloring solution or obtainable by a process comprising the step of firing the dental ceramic articles.

24 Claims, 2 Drawing Sheets

(51) Int. Cl.
  *A61K 6/02* (2006.01)
  *C04B 41/50* (2006.01)
  *C04B 41/00* (2006.01)
  *C04B 41/85* (2006.01)
  *A61K 6/00* (2006.01)
  *C04B 111/00* (2006.01)
  *C04B 111/82* (2006.01)

(52) U.S. Cl.
  CPC ..... *C04B 41/85* (2013.01); *C04B 2111/00836* (2013.01); *C04B 2111/82* (2013.01)

(58) Field of Classification Search
  CPC ......... C04B 35/00; C04B 35/10; C04B 35/48; C04B 41/4535; C04B 2111/00836; C04B 2111/82; C04B 41/85; A61K 6/0002
  USPC ...................................... 106/35, 14.29, 741
  See application file for complete search history.

(56) References Cited

U.S. PATENT DOCUMENTS

| | | | |
|---|---|---|---|
| 3,027,331 | A | 3/1962 | Schrewelius |
| 3,141,780 | A | 7/1964 | Simon et al. |
| 4,047,970 | A | 9/1977 | Morriss et al. |
| 4,189,325 | A | 2/1980 | Barrett et al. |
| 4,546,006 | A | 10/1985 | Ohno et al. |
| 4,550,030 | A | 10/1985 | Ohi et al. |
| 4,681,633 | A | 7/1987 | Watanabe et al. |
| 4,772,436 | A | 9/1988 | Tyszblat |
| 4,828,117 | A | 5/1989 | Panzera et al. |
| 4,877,402 | A | 10/1989 | Hirabayashi et al. |
| 5,011,403 | A | 4/1991 | Sadoun et al. |
| 5,091,033 | A | 2/1992 | Nakabayaski et al. |
| 5,106,303 | A | 4/1992 | Oden et al. |
| 5,219,805 | A | 6/1993 | Yoshida et al. |
| 5,250,352 | A | 10/1993 | Tyszblat |
| 5,263,858 | A | 11/1993 | Yoshida et al. |
| 5,447,967 | A | 9/1995 | Tyszblat |
| 5,565,152 | A | 10/1996 | Oden et al. |
| 5,618,585 | A | 4/1997 | Hechler et al. |
| 5,869,548 | A | 2/1999 | Ikushima et al. |
| 6,042,884 | A | 3/2000 | Klein et al. |
| 6,106,747 | A | 8/2000 | Wohlwend |
| 6,114,054 | A | 9/2000 | Klein et al. |
| 6,132,672 | A | 10/2000 | Vignali |
| 6,464,765 | B1 | 10/2002 | Garcia et al. |
| 6,709,694 | B1 | 3/2004 | Suttor et al. |
| 6,713,421 | B1 | 3/2004 | Hauptmann et al. |
| 6,756,421 | B1 | 6/2004 | Todo et al. |
| 6,786,994 | B2 | 9/2004 | Williams et al. |
| 7,432,037 | B2 | 10/2008 | Suzuki et al. |
| 2004/0119180 | A1 | 6/2004 | Frank et al. |
| 2006/0117989 | A1 | 6/2006 | Hauptmann et al. |
| 2007/0062410 | A1 | 3/2007 | Thiel et al. |
| 2008/0286718 | A1 | 11/2008 | Franke et al. |
| 2010/0047438 | A1 | 2/2010 | Hauptmann et al. |
| 2010/0062398 | A1 | 3/2010 | Schechner et al. |

FOREIGN PATENT DOCUMENTS

| | | |
|---|---|---|
| DE | 2 117 449 A1 | 10/1972 |
| DE | 3109927 | 9/1982 |
| DE | 3424777 | 1/1985 |
| DE | 3435181 | 8/1985 |
| DE | 3435182 | 8/1985 |
| DE | 34 35 348 C2 | 3/1986 |
| DE | 4207179 A1 | 9/1992 |
| DE | 4320072 | 5/1994 |
| DE | 37 51 344 T2 | 3/1996 |
| DE | 19619165 | 9/1997 |
| DE | 19619168 | 10/1997 |
| DE | 196 25 236 A1 | 1/1998 |
| DE | 19625236 | 7/1998 |
| DE | 19904522 | 8/2000 |
| DE | 10052203 A1 | 4/2001 |
| EP | 0047873 A2 | 3/1982 |
| EP | 0230534 | 5/1987 |
| EP | 0329565 | 8/1989 |
| EP | 0389461 B1 | 11/1993 |
| EP | 0 803 241 A2 | 10/1997 |
| EP | 0816305 A1 | 1/1998 |
| EP | 0 824 897 A2 | 2/1998 |
| EP | 1486476 | 11/2005 |
| FR | 2 781 366 A1 | 1/2000 |
| GB | 421872 | 1/1935 |
| JP | 62-158183 | 7/1987 |
| JP | 214866 | 6/1988 |
| JP | 3-5366 A | 1/1991 |
| JP | 3-170148 A | 7/1991 |
| JP | 3-198841 | 8/1991 |
| JP | 4-280864 A | 10/1992 |
| JP | 2571646 | 10/1992 |
| JP | 06-345566 | 12/1994 |
| JP | 8-33650 A | 2/1996 |
| JP | 08-337484 | 12/1996 |
| JP | 9-110563 | 4/1997 |
| JP | 9-142966 | 6/1997 |
| JP | 2002308620 | 10/2002 |
| JP | 2002348496 | 12/2002 |
| JP | 2004-149587 | 5/2004 |
| JP | 2005-281414 | 10/2005 |
| JP | 2005-298596 | 10/2005 |
| JP | 2006002100 | 1/2006 |
| JP | 2006-176762 | 7/2006 |
| JP | 2007-015946 | 1/2007 |
| JP | 2007-031288 | 2/2007 |
| JP | 2007-039475 | 2/2007 |
| JP | 2007-131841 | 5/2007 |
| WO | WO 96/29951 A2 | 10/1996 |
| WO | WO 97/38952 A1 | 10/1997 |
| WO | WO 97/49650 A1 | 12/1997 |
| WO | WO 00/46168 A1 | 8/2000 |
| WO | WO 03/076521 A1 | 9/2003 |
| WO | WO 2004/110959 | 12/2004 |
| WO | WO 2006/108677 A1 | 10/2006 |
| WO | WO 2008/098157 | 8/2008 |

OTHER PUBLICATIONS

Hollemann-Wiberg, Lehrbuch der Anorganischen Chemie, 101 Aulage, de Gruyter, Berlin, New York, 1995, pp. 1838-1841.
Search Report for PCT/US2008/069595.
Written Opinion for PCT/US2008/069595.
Ext. European Search Report for EP 07112920.9-2111.
Todorosxky et al., "Preparation and Charactgerization of Yttrium-iron Citric Acid Complexes" *Croatica Chemica Acta*, vol. 75, No. 1, 2002, pp. 155-164, XP002440842.
Written Opinion of the ISA for International Application No. PCT/US2008/053393, pp. 5.
Search Report for PCT/US2008/053393.
Ext. European Search Report for EP 07002726.
Search Report for PCT/EP00/00910.
Search Report from PCT/EP2004/006220; 3 pgs.
Written Opinion from PCT/EP2004/006220.
Cales, "Colored Zirconia Ceramics for Dental Applications," *Bioceramics*, 1998;11: 3 sheets.
Rieger, "Aluminum and Zirconium Oxide Ceramics in Medicine," *Industrie Diamanten Rundschau*, 1993;IDR 2:pp. 1-7.
Nakumura, T. Et al., "Clinical Applications of a Newly Developed Hybrid Ceramic Composite for Posterior Prostheses," Quintessence of Dental Technology (1999), pp. 83-93.
"Masters in Concert: Interview" Dr. Gerard Chiche and Mr. Hitoshi Aoshima, Quintessence of Dental Technology, vol. 20 (1997), p. 10-20.
Mutobe, Y. Et al., "In Harmony with Nature: Esthetic Restoration of a Nonvital Tooth with IPS-Empress All-Ceramic Material," Quintessence of Dental Technology, vol. 20 (1997), pp. 83-106.
"VITA-Hi-Ceram Working Instructions" (pub'd Aug. 1990).
"The Vitadur Technique, Working Instructions," 5th ed. (pub'd Sep. 1990).

(56) References Cited

OTHER PUBLICATIONS

Naylor, W., "Introduction to Metal Ceramic Technology" (1992), pp. 138-139.
McLean, J., "The Science and Art of Dental Ceramics,"Monographs III and IV (2nd printing, 1978) pp. 7, 26.
Aoshima, H., "Aesthetic All-Ceramic Restorations: The Internal Live Stain Technique," PP&A, vol. 9, No. 8 (1997) pp. 861-868.
Craig, R., "Restorative Dental Materials," 7th Edition, Chapter 17, pp. 432-449.
McLean, "The Science and Art of Dental Ceramics", vol. 1, 1979, pp. 7, 26.
McLean, "The Science and Art of Dental Ceramics", vol. 2, 1980, pp. 7, 26.
Yamamoto, M., "Metal Ceramics: Principles and Methods of Makoto Yamamoto", 1985.
Sorensen, J. et al., "In-Ceram Fixed Partial Dentures: Three-Year Clinical Trial Results," Journal of the California Dental Association, vol. 26, No. 3 (Mar. 1998) pp. 207-214.
Fulmer, J. et al., "Tensile, Impact and Fatigue Performance of a New Water Atomized Low-Alloy Powder—Ancorsteel 85 HP," (1990) pp. 1, 4.
Ocana, M. Et al., "Preparation by Hydrolysis of Aerosols and Colour Properties for Cr-Doped and Co-Doped Zircon Powders," Journal of the European Ceramic Society 18 (1998) pp. 821-830.
"Ceramic Products Manufacturing," (1996) 11.7-1-11.7-13.
Industrie Diamanten Rundschau IDR Feb. 1993 "Aluminum and Zirkonoxidkeramik in der Medizin".
Pamphlet relating to the Cerec System—"Okonomie durch Technologie".
Pamphlet relating to the Procera system.
ASTM D2805.
Hawley's Chemical Dictionary, 13th Ed., pp. 852-853.
Table of Periodic Properties of the Elements, Sargent-Welch Scientific Company, Illinois 1980.
Expert Report of Russell A. Giodano (Feb. 27, 2008) (26 pgs).
Defendant's Vita Zahnfabrik H. Rauter Gmbh & Co. KG and Vident, Inc.'s Prior Art Statement.
Defendants' Proposed Claim Constructions (Case No. 05 CV 1875 ADM/JJG).
Defendants' Identification of Claim Terms That Require Construction (Case No. 05 CV 1875 ADM/JJG).
Disputed Claim Terms (Civil No. 05 1875 (ADM/JSM)).
Joint Claim Construction Statement (Civil No. 05 1875 (ADM/JSM).
Defendants' Responses to First Set of Interrogatories (Nos. 1-10) (Case No. 05CV1875 ADM/JJG).
Defendants' Claim Chart (Case No. 05CV1875 ADM/JJG).
Defendants Vita Zahnfabrik H. Rauter Gmbh & Co. KG and Vident, Inc's Supplemental responses to Plaintiffs 3M Company and 3M Innovative Properties Company's Interrogatories Nos. 1, 2 and 3 (Case No. 05CV1875 ADM/JJG).
Rebuttal Expert Report of Kenneth J. Anusavice Regarding the Validity of U.S. Pat. No. 6,709,694 (Case No. 05CV1875 ADM/JSM).
Plaintiffs' Prior Art Statement (Case No. 05CV1875 ADM/JSM).
Plaintiffs' Supplemental Answers and Objections to Defendants' First Set of Interrogatories (Nos. 1-13) (Case No. 05CV1875 ADM/JSM).
Defendants' Response to Request for Admissions (Nos. 1-50) (Case No. 05CV1875 ADM/JJG).
Filser et al., "All-Ceramic Dental Bridges by Direct Ceramic Machining (DCM)," *Materials in Medicine, Materials Day*, May 1998; pp. 165-189. From opposition of DE Patent No. 199 04 5223.
"Lösung (Chemie)," Wikipedia [online], Wikimedia Foundation, Inc., San Francisco, CA [retrieved on Sep. 12, 2002]. Retrieved from the Internet:<URL://http://de.wikipedia.org/wiki/L%C3%B6sung_(Chemie)>; 4 pgs.

Foerst, W., *Ullmanns Encyklopädie der technischen Chemie, 9. Band Isocyanate bis Kohlenstoff*, München, Germany, 1957, cover page, title page, and pp. 436-446. From opposition of DE Patent No. 199 04 5223.
Shanefield, D. J., *Organic Additives and Ceramic Processing*, Boston, MA, 1995; cover page, title page, and table of contents; 9 pgs. From opposition of DE Patent No. 199 04 5223.
Andersson et al., "A new all-ceramic crown: A dense-sintered, high-purity alumina coping with porcelain," *Acta Odontol Scand.*, 1993; 51:59-64. From opposition of DE Patent No. 199 04 5223.
Åse, *Water Colour on Porcelain: A Guide to the Use of Water-Soluble Colourants*, Norway 1989; 64 pgs. From opposition of DE Patent No. 199 04 5223.
Albano et al., "Mullite/SiAION/Alumina Composites by Infiltration Processing," *J. Am. Ceram. Soc.*, 1997; 80(1):117-124. From opposition of DE Patent No. 199 04 5223.
Marple et al., "Mullite/Alumina Particulate Composites by Infiltration Processing," *J. Am. Ceram. Soc.*, 1989; 72(11):2043-2048. From opposition of DE Patent No. 199 04 5223.
"ProCAD by Ivoclar—Gebrauchsinformation," Ivoclar, Schaan, Liechtenstein, 1998; 6 pgs. From opposition of DE Patent No. 199 04 5223.
Kurbad et al., "Cerec inLab—State of the art," *Quintessenz Zahntech*, 2001, 27(9):1056-1074. From opposition of DE Patent No. 199 04 5223.
Schumann, "Cercon® in der Anwendung," *Quintessenz Zahntech*, 2002, 28(5):509-517. From opposition of DE Patent No. 199 04 5223.
Loos et al., "Transluzentes Zirkoniumdioxid and optimierte Färbelösung," *Digital Dental News*, 2009, 3:20-27.
Kratochvil, "Vorzüge einer Zirkonoxidkrone," *cad/cam*; 2006; 5:71-73. From opposition of DE Patent No. 199 04 5223.
Pospiech et al., "Vom Zirkonoxidgerüst zur Lava-Vollkeramik," *dental-labor, L*, 2002:59-67. From opposition of DE Patent No. 199 04 5223.
Falbe et al., *Römpp Chemi Lexikon*, Stuttgart, Germany, 1995; title page and pp. 2537-2540. From opposition of DE Patent No. 199 04 5223.
"Zahnersatz," Wikipedia [online], Wikimedia Foundation, Inc., San Francisco, CA [retrieved on 10-04-20]. Retrieved from the Internet: <URL:http://de.wikipedia.org/w/index.php?title=Zahnersatz&printable=yes>;10 pgs. From opposition of DE Patent No. 199 04 5223.
"Ausbildung," datasheet [online]. Zahnlaboratorium, Berlin, Germany, 2002 [retrieved on Sep. 4, 2003]. Retrieved from the Internet:<URL:http://www.zahnlaboratorium.de/flausb.htm>; 4 pgs. From opposition of DE Patent No. 199 04 5223.
"Verordnung über die Berufsausbildung zum Zahntechniker/zur Zahntechnikerin," *Bundesgesetzblatt Jahrnang*, 1997; 87:3182-3190. From opposition of DE Patent No. 199 04 5223.
Heuschkel, "Dentalkeramik," *ABC Keramik*, Leipzig, Germany, 1990; title page and pp. 82-83; 2 pgs. From opposition of DE Patent No. 199 04 5223.
Vichi et al., "Color related to ceramic and zirconia restorations: A review," *Dental Materials*, 2011; 27:97-108. From opposition of DE Patent No. 199 04 5223.
"Zirkoniumdioxid: Info Zahntechniker" datasheet [online]. Arbeitsgruppe Vollkeramik München, [retrieved on Sep. 3, 2012]. Retrieved from the Internet:<URL:www.zirkondioxid.de/index.php?id=14>; 6 pgs. From opposition of DE Patent No. 199 04 5223.
"Zirkonrohlinge maßgeschneidert für Ihr Frässystem" datasheet [online]. <URL:http://www.white-peaks-dental.de/blands.php>; 1 page. "CopranColor/CopranUltra-T Color" datasheet [online]. <URL:http://www.white-peaks-dental.de/copran-zr-color.php>; 2 pgs. White Peaks Dental, Essen, Gemiany, 2007 [retrieved on Sep. 3, 2012]. "Verarbeitungsempfehlung & technische Daten Copran Color / Copran Ultra-T Color," White Peaks Dental, Essen, Germany, 2008; 2 pgs. "Sicherheitsdatenblatt gemäß EG—Richtlinie 2001/58/EG," White Peaks Dental, Essen, Germany, 2012; 5 pgs. From opposition of DE Patent No. 199 04 5223.
"In-Ceram YZ Coloring Liquid Light Set," datasheet [online]. Dental CADCAM E.K., Mannheim, Germany, 2011 [retrieved on Sep. 3, 2012]. Retrieved from the Internet:<URL:http://www.

(56) References Cited

OTHER PUBLICATIONS dentalcadcam.de/dentalshop/in-ceram-yz-coloring-liquid-light-set. html>; 1 page. From opposition of DE Patent No. 199 04 5223.

"DD Bio Z Coloring liquids—for perfect color results," datasheet [online]. Dental Direkt, Spenge, Germany, 2009 [retrieved on Sep. 3, 2012]. Retrieved from the Internet:<URL:http://www.dentaldirekt.com/products/zro2-colouring-liquids.html>; 1 page. "DD Color Processing Instructions," 2011, Spenge, Germany; 3 pgs. "DD Bio high translucent zirconia," Spenge, Germany, 4 pgs. "DD BioZX2 paint," 2012, Spenge, Germany; 19 pgs. From opposition of DE Patent No. 199 04 5223.

"Zirkonzahn—Colour Liquid Waterbased," datasheet [online]. Zirkozahn GmbH, Gais, Germany, 2003 [retrieved on Sep. 3, 2012]. Retrieved from the Internet:<URL:http://www.zirkonzahn.com/de/produkte/colour-liquids/colour-liquid-waterbased>; 7 pgs. "Einfärben von Zirkon mit Colour Liquid Prettau® Aquarell," Zirkonzahn GmbH, Gais Germany; 4 pgs. From opposition of DE Patent No. 199 04 5223.

"ceramill zolid," Amann Girrbach, Koblach, Austria, 2006-2013; 4 pgs. "ceramill liquid," Amann Girrbach, Koblach, Austria, 2006-213; 4 pgs. "Framework Management Analog," Amann Girrbach, Koblach, Austria, 2006-2013; 64 pgs. From opposition of DE Patent No. 199 04 5223.

"Advanced technology for your perfect smile!" isel®, Houdan, France, 2010; 20 pgs. From opposition of DE Patent No. 199 04 5223.

"Teamziereis Newsletter 'Konzept Zukunftslabor,'" TeamZiereis GmbH, Engelsbrand, Germany, 2011; 4 pgs. "Colibri Colouring Liquid Arbeitsanleitung," TeamZiereis GmbH, Engelsbrand, Germany; 3 pgs. From opposition of DE Patent No. 199 04 5223.

"inCoris TZI," brochure, 2011, Behsheim, Germany; 20 pgs. From opposition of DE Patent No. 199 04 5223.

"Einfärbelösung / Umlufttrockner," datasheet ]online]. imes-icore GmbH, Eiterfeld, Germany, 2012. Retrieved from the Internet:<URL:http://www.imes-icore.de/branchen/page.php?id=105&title-Einf%C3%Arbel%C3%B6sung+2F+_Umlufttrockner>; 1 page. "Gebrauchsanweisung CORiSHADE," brochure. imes-icore GmbH, Eiterfeld, Germany, 2010; 2 pgs. From opposition of DE Patent No. 199 04 5223.

"3M ESPE Dental Profressionals: 3M Licenses Dental Ceramic Coloring GmbH; Files Patent Infringement Suit," datasheet [online]. 3M ESPE, St. Paul, MN, 2012 [retrieved on Sep. 13, 2012]. Retrieved from the Internet:<URL:http://solutions.3m.com/wps.portal/3M/en_US/3M-ESPE-NA/dental-professionals>; 2 pgs. From opposition of DE Patent No. 199 04 5223.

"Versuchsbericht," 14 pgs. From opposition of DE Patent No. 199 04 5223.

"3M and Ivoclar Vivadent Settle Dental Zirconia Coloring Patent Suit," *3M Newsroom*, 3M, St. Paul, MN, 2012 [online]. Retrieved from the Internet: <URL:http://news.3m.com/press-release/company/3m-and-ivoclar-vivadent-settle-dental-zirconia-coloring-patent-suit>; 1 page. From opposition of DE Patent No. 199 04 5223.

\* cited by examiner

COLOURING SOLUTION FOR DENTAL CERAMIC ARTICLES AND RELATED METHODS

CROSS REFERENCE TO RELATED APPLICATIONS

This application is a national stage filing under 35 U.S.C. § 371 of PCT/US2008/069595, filed Jul. 10, 2008, which claims priority to EP Application No. 07112920.9, filed Jul. 23, 2007, the disclosure of which is incorporated by reference in its/their entirety herein.

FIELD OF THE INVENTION

The invention relates to a colouring solution for dental ceramic articles, such as dental frameworks, and a process for using the colouring solution in the dental field. More specifically the invention relates to a colouring solution comprising a) a solvent, and b) a colouring agent comprising a mixture of metal ions.

BACKGROUND OF THE INVENTION

Dental ceramic frameworks can either be coloured by incorporating pigments into the ceramic material or using metal salts containing solutions which are to be applied on the surface of partially sintered dental ceramic framework.

In this respect DE 196 19 168 A1 describes a ceramic colouring solution consisting essentially of water and a palladium containing compound dissolved therein. The solution might further contain co-solvents such as alcohols, glycols, glycol ether or polyethylene glycol.

WO 2004/110959 (corresponding to US 2006/117989 A1) relates to a colouring solution for ceramic framework. The solution comprises a solvent, a metal salt and polyethylene glycol having a molecular weight in the range of 1.000 to 200.000.

DE 196 19 165 C1 describes a process for colouring ceramic paving stone with an aqueous solution containing Ti and Fe components together with complexing agents.

WO 00/46168 A1 (corresponding to U.S. Pat. No. 6,709,694 B1) refers to colouring ceramics by way of ionic or complex-containing solutions containing defined concentrations of at least one salts or complexes of the rare earth elements or of the elements of the subgroups.

The solution might contain additives like stabilizers, complex builders, pigments and beating additives.

SUMMARY OF THE INVENTION

The invention relates to a colouring solution for colouring dental ceramic articles, including dental frameworks. The colouring solution comprises:
a solvent and
a colouring agent or agents, comprising
 rare earth element metals or ions being present in the solution in an amount of at least about 0.05 mol/l solvent,
 and transition metals or ions being present in the solution in an amount of about 0.00001 to about 0.05 mol/l solvent.

The invention also relates to a process for colouring dental ceramic articles, including dental frameworks. The process comprises the steps of:
providing a colouring solution as described herein and
providing a dental ceramic framework,
treating the ceramic article (e.g. framework) with the colouring solution,
optionally drying the treated ceramic article (e.g., framework) and
optionally firing the treated ceramic article (e.g., framework).

In another aspect, the invention relates to dental ceramic article, such as a dental framework, treated either with the colouring solution or obtainable by a process comprising the step of firing the dental ceramic article.

In a further aspect, the invention relates to a process of using a colouring solution comprising a solvent and a colouring agent comprising rare earth element metals or ions and mixtures thereof, the metal ions being present in an amount of at least about 0.05 mol/l solvent for reducing the sintering distortion of dental ceramic articles (e.g., framework) during or after a sintering step.

Presintered dental ceramic articles (e.g. frameworks) treated with the inventive colouring solution usually have a tooth-like colour after a sintering step and show less distortion after a sintering step.

Other embodiments, features and advantages of the present invention will be apparent from the following detailed description, drawings, and claims.

DEFINITIONS

The term "dental article" within the meaning of the invention is to be understood as any article based on or comprising a ceramic material, an article which can be used in the dental area including dental laboratories.

The term "dental ceramic framework" within the meaning of the invention is to be understood as any ceramic framework which can be used in the dental field. In this respect, the dental ceramic framework shall have sufficient strength. Examples include inlays, onlays, crowns, abutments and bridges (including 2, 3, 4, 5, 6, 7 or even 8 parts bridges) and implants. The dental ceramic framework has usually a 3-dimensional inner and outer surface including convex and concave structures. Compared to other ceramic framework such as pottery or paving stones, the dental ceramic framework is small and filigree. The thickness of the dental ceramic framework can vary from very thin, e.g. at the edges and rims (below about 0.1 mm) to considerably thick, e.g. in the biting area (up to about 7 mm).

A "solvent" within the meaning of the invention is any solvent or liquid which is able to at least partially dissolve the colouring agent.

A "colouring agent" within the meaning of the invention is any agent, which is able to lead to a colour change of a dental ceramic framework either right after treatment of the ceramic framework with the colouring agent or after a firing step of the treated dental ceramic framework.

A "complexing agent" within the meaning of the invention is any agent which is able to form complexes with the colouring agent.

A "complex", also known as coordination compound, in chemistry usually is used to describe molecules or ensembles formed by the combination of ligands and metal ions. Originally, a complex implied a reversible association of molecules, atoms, or ions through weak chemical bonds. As applied to coordination chemistry, this meaning has evolved. Some metal complexes are formed virtually irreversibly and many are bound together by bonds that are quite strong.

The ions or molecules surrounding the metal are called ligands. Ligands are generally bound to a metal ion by a coordinative bonding (donating electrons from a lone electron pair to the Lewis acidic metal center), and are thus said to be coordinated to the ion. Within the meaning of the present invention, those ligands are referred to as "coordinating ligands".

The areas of coordination chemistry can be classified according to the nature of the ligands. Complexes can be classified as "classical" or "organometallic" complexes.

Classical (e.g. so-called "Werner Complexes"): Ligands in classical coordination chemistry bind to metals, almost exclusively, via their "lone pairs" of electrons residing on the main group atoms of the ligand, such as [Co(EDTA)]$^-$ or [Co(NH$_3$)$_6$]Cl$_3$.

Organometallic Chemistry: Ligands are organic (alkenes, alkynes, alkyls) as well as "organic-like" ligands, such as (C$_5$H$_5$)Fe(CO)$_2$CH$_3$. It is assumed that those ligands form a direct covalent bond to the metal centre.

The term "amount sufficient to dissolve" within the meaning of the invention describes the amount of an agent needed to fully dissolve a certain substance in a certain solvent so that a storage stable composition can be obtained. Storage stable means that the solution stored for a certain period of time at ambient conditions (e.g. at least 3 month, 23° C.) remains stable without decomposition of the solution or precipitation of single or multiple components. The agent might be used in an under-stoichiometric amount (e.g. 0.1 mol agent, 0.5 mol substance), equal amount (e.g. 0.1 mol agent, 0.1 mol substance), or even in excess (e.g. 0.2 mol agent, 0.1 mol substance). The time needed to dissolve the substance is not particularly limited, however, the dissolution should occur within a reasonable time (e.g. about 5 min to about 24 h) using common equipment like mechanical stirrers and heaters.

Rare earth element metals and/or of the subgroups of the rare earth elements include La, Ce, Pr, Nd, Sm, Eu, Gd, Tb, Dy, Ho, Er, Tm, Yb and Lu.

Transition metals of the groups IIIA, IVA, VA, VIA, VIIA, VIIIA, IB, IIB (according to the former IUPAC classification) comprise the metals listed in the columns of the Periodic Table of Elements starting with the elements Sc, Ti, V, Cr, Mn, Fe, Co, Ni, Cu and Zn and the metals listed below those elements. According to the new IUPAC classification these columns are numbered as 3, 4, 5, 6, 7, 8, 9, 10, 11 and 12. According to the invention, the term "transition metals or ions" do not comprise "rare earth element metals or ions".

The terms "metal" or "metal ions" or "metal cations" are used interchangeably depending on the context and the present conditions. Depending on the solution and the presence or absence of other components (such as complexing agents), the metal can be present as such (i.e. in pure element form) or as ion or cation usually having a charge of +1, +2, +3 or +4.

A dental ceramic article or framework is classified as "presintered" within the meaning of the invention if the dental ceramic framework has been treated with heat (temperature range from about 900 to about 1100° C.) for about 1 to about 3 hours to such an extend that the raw breaking resistance (Weibull strength Sigma 0) of the dental ceramic article or framework is within a range of about 15 to about 55 MPa or about 30 to about 50 MPa (measured according to the "punch on three ball test" (biaxial flexural strength) described in DIN EN ISO 6872, edition March 1999, with the following modifications: diameter of steel ball: 6 mm; diameter of support circle: 14 mm; diameter of flat punch: 3.6 mm; diameter of sample disc: 25 mm, thickness of sample disc: 2 mm; no grinding and polishing of samples.)

A presintered dental ceramic article or framework typically has a porous structure and its density (usually 3.0 g/cm$^3$ for an Yttrium stabilized ZrO$_2$ ceramic) is less compared to a completely sintered dental ceramic framework (usually 6.1 g/cm$^3$ for an Yttrium stabilized ZrO$_2$ ceramic). The diameter of the pores can be in a range of about 50 nm to about 150 nm (corresponding to about 5 to about 15 Å). A typical pore diameter is about 120 nm.

The terms "sintering" or "firing" are used interchangeably. A presintered ceramic framework shrinks during a sintering step, that is, if an adequate temperature is applied. The sintering temperature to be applied depends on the ceramic material chosen. For ZrO$_2$ based ceramics a typical sintering temperature range is about 1200° C. to about 1500° C. Al$_2$O$_3$ based ceramics are typically sintered in a temperature range of about 1300° C. to about 1700° C.

A dental ceramic framework is classified as "absorbent" within the meaning of the invention if the dental ceramic framework is able to absorb a certain amount of a liquid, comparable to a sponge. The amount of liquid which can be absorbed depends e.g. on the chemical nature of the dental ceramic framework, the viscosity of the solvent, the porosity and pore volume of the dental ceramic framework. E.g. a presintered dental ceramic article, that is an article which has not been sintered to full density is able to absorb a certain amount of liquid.

The term "sintering deformation" within the meaning of the invention describes the change of the geometrical shape of a dental ceramic framework which might occur during a sintering process caused e.g. by inhomogeneity of the material the dental ceramic framework is made of. A sintering deformation of a dental ceramic framework might occur only in one dimension or in two or in three dimensions. The sintering deformation can be measured comparing the shape of the dental ceramic framework before and after a sintering process. The difference in shape can either be measured by an accurate geometrical measurement of the dental ceramic framework using e.g. a microscope or by examining the precision fit of a dental ceramic framework on a model as described in the text below. A test which can be used for the evaluating of the deformation of the coloured ceramic framework after sintering is as follows: A rod-shaped sample is processed similar to a 3M ESPE Lava™ bridge (milling, dyeing and sintering) with a commercially available 3M ESPE Lava™ equipment. The presintered sample (3M ESPE Lava™ Frame blank for bridges) is milled, thereafter the dust is removed with microbrushes and compressed air. The milled sample is dipped in the colouring solution for about two minutes. After that any excessively adhering dyeing liquid is removed with an absorbent paper. The sample is placed on two 3M ESPE Lava™ sintering supports (20 mm distance) for posterior bridges (curved platinum wire). The proportion between sample length and distance between the wires is like the sintering of a bridge. The firing can be done in a 3M ESPE Lava™ Therm furnace with the standard sintering program. After sintering the deformation of the samples is measured with a profile projector. A more detailed description is given in the Examples section.

The term "precision fit" within the meaning of the invention describes the exactness a dental ceramic framework fits to a prepared model, i.e. whether to which extend the internal surface of dental ceramic framework matches with the external surface of tooth structure such as a prepared tooth stump. Especially with regard to wide spanning dental bridges this can be an important feature a dental ceramic framework should fulfil to avoid a move back-and-force or up-and-down of the bridge to be fixed on two tooth stumps.

A dental ceramic framework can be characterized as "homogeneously coloured" within the meaning of the invention, if no colour spots can be identified with the human eye on the surface of the dental ceramic framework after the sintering process. More precisely, this can be proven by measuring the L*a*b* values according to DIN 6174 (Section 2) using a commercially available Hunter Lab System applying the respective instructions of use. Further hints to this measuring system can be found in U.S. Pat. No. 6,756,421 column 4, lines 26 to 55.

A dental ceramic framework has a "tooth like colour" within the meaning of the invention if its colour can be classified by the VITA™ shading system under daylight conditions known to the dental technician.

"Ambient conditions" within the meaning of the invention mean the conditions which the inventive solution is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are adjusted to about 23° C. and about 1013 mbar.

A composition or solution is "essentially free of" a certain component within the meaning of the invention, if the composition or solution does not contain said component as an essential feature. Thus, said component is not willfully added to the composition or solution either as such or in combination with other components or ingredient of other components. A composition being essentially free of a certain component usually contains the component in an amount of less than about 1 wt.-% or less than about 0.1 wt.-% or less than about 0.01 wt.-% (or less than about 0.05 mol/l solvent or less than about 0.005 mol/l solvent or less than about 0.0005 mol/l solvent) with respect to the whole composition. Ideally the composition or solution does not contain the said component at all. However, sometimes the presence of a small amount of the said component is not avoidable e.g. due to impurities.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

DETAILED DESCRIPTION OF THE INVENTION

Figure 1:
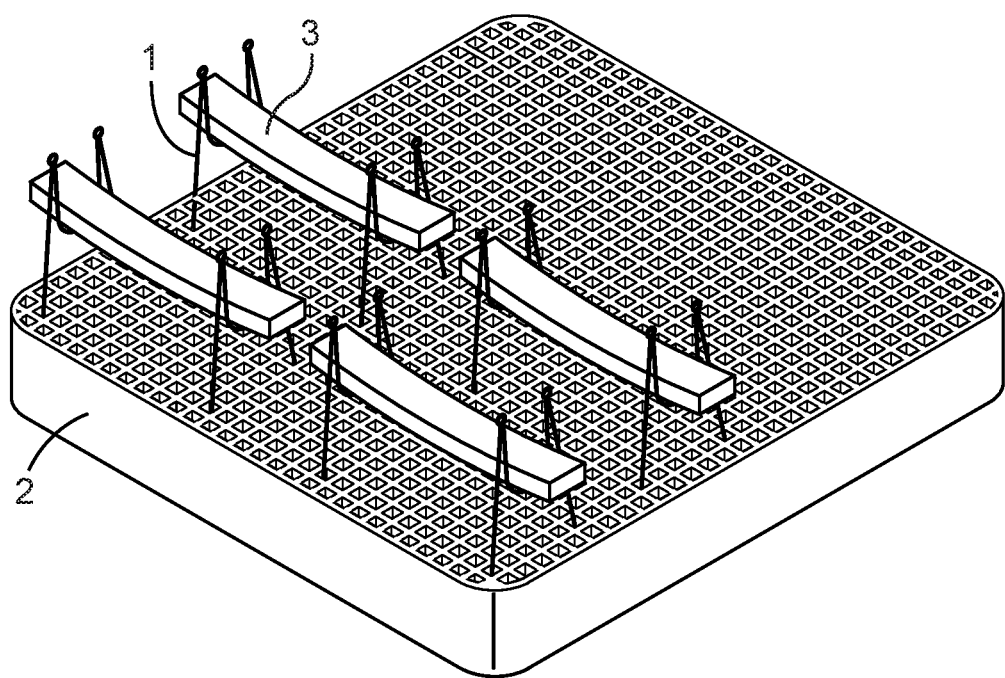
FIG. 1 shows four pieces of distorted sintered dental ceramic articles (e.g., frameworks) on supporting structures.

It has been found that under certain conditions dental ceramic articles treated with the inventive colouring solution sometimes shows less defects (e.g. less sintering deformation) after a sintering or firing process compared to dental ceramic articles treated with commercially available colouring solutions.

Without wishing to be bound to a certain theory it is believed that the size of the metal or metal ion used in the inventive colouring solution has an influence on the extent of distortion the dental ceramic article might show after a firing process.

It is believed that the distribution of metal ions having a large ionic radius in the dental ceramic article is better compared to metal ions having a smaller ionic radius. This might also lead to a more homogeneous colouring of the dental ceramic article.

In view of the fact that the pore diameter of the presintered dental ceramic article is in a range of about 50 to about 150 nm, the pore diameter is not a limiting factor for the ions being present in the colouring solution. However, the larger the ionic diameter of the ions being present in the colouring solution is, the more coordinating ligands the ion can have. Typically Fe has a coordination number of 6, whereas rare earth element metal ions might have a coordination number of 8, 9, 10 or even 12 (e.g. in oxides). It is believed that the number of coordinating ligands a metal can have, has an influence on the stability of the area surrounding the metal.

Tetragonal and cubic zirconia ($ZrO_2$) usually have a so-called Flurorite Type Structure. In such a structure the cations are surrounded by 8 anions in the first coordination sphere.

Thus, a dental ceramic article comprising tetragonal or cubic zirconia has areas in the ceramic structure in which rare earth element metals or ions with a larger atomic or ionic radius more or less might fit.

Without wishing to be bound to a certain theory, it is believed that the metals or ions having a large atomic or ionic radius might help to improve the distortion of the dental ceramic article after a firing step and that the metals or ions having a smaller atomic or ionic radius contribute to the visually appearance of the coloured dental ceramic article after a firing step.

Thus, using the inventive colouring solution it can be possible to improve the precision fit of wide spanning dental frameworks (e.g. a dental bridge with more than 3, 4 or 5 units) on prepared tooth structures.

This possible reduction in distortion of the sintered dental ceramic article might also simplify the whole sintering process. With respect to some embodiments of the invention, it can be possible to sinter wet items of the dental ceramic framework in the furnace without a significant time delay, e.g. without the need for an additional drying step which usually has to be carried out with conventional commercially available shading liquids. A drying step may last for up to about 3 h. When using the inventive colouring solution a reduction of the sintering cycle time combined with cost savings seems to be achievable. Using solvents having a comparable low vapor pressure like organic solvents such as hydrocarbons might even further reduce the cycle time.

Moreover, in certain embodiments the dental ceramic framework having been treated with the inventive colouring solution shows a tooth-like colour after a firing step.

Not mandatory, but generally desirable is to have a stable colouring solution that can be stored for many months. Certain embodiments of the inventive colouring solution usually remain stable over a considerable long period of time (at least about 4 weeks to more than about 12 months under ambient conditions). They typically do not show any visible precipitation of the colouring agent during storage at ambient conditions (23° C., normal pressure).

According to certain implementations of the present invention the counter ions and/or complexing agents which can be used are purely organic substances and thus only contain elements like H, N, O, C, etc., which can be completely burned without leaving any detrimental residues during the sintering process. The thermal disintegration would mainly yield only non-corrosive gases like water, nitrogen or carbon dioxide.

The presence of a huge amount of halogen ions might cause problems due to the disintegration of the colouring solution at high temperatures during the sintering process. The disintegration may lead to the formation of aggressive substances like chlorine or HCl in the sinter furnace. Without wishing to be bound by any theory, those gases might cause corrosion at the surface of the heating elements and yield other volatile compounds such as $MoCl_6$ or $FeCl_3$ due to the reaction with the material of the heating elements (which may contain e.g. $MoSi_2$ and traces of iron). In some cases, the resulting reaction products may condense or decompose on the surface of the dental ceramic article to be sintered thus causing discoloration on the surface of the sintered dental ceramic framework after cooling.

The inventive colouring solution comprises a solvent. The solvent should be able to at least partially dissolve the components of the composition, especially the colouring agent(s) selected. Typical solvents which can be used either alone or in admixture include water, alcohols like methyl alcohol, ethyl alcohol, iso-propyl alcohol, n-propyl alcohol, polar aprotic liquids like ketones such as acetone, ethylacetate and mixtures of water with alcohols and/or ketones. Preferred solvents which can be used in pure form include e.g. water and alcohols. Examples of useful mixtures of solvents include water and ethyl alcohol. These solvents are especially useful for polar complexes. For nonpolar complexes, solvents like ethers (including diethylether, THF) or hydrocarbons (including pentane, hexane, heptane and octane; including its n-, sec-, tert-isomers) can be used.

The amount of solvent used is not particularly limited unless the result to be achieved cannot be obtained. A typical colouring solution according to the invention contains at least about 60 wt.-% solvent or least about 75 wt.-% solvent or least about 90 wt.-% solvent with respect to the weight of the whole composition.

The colouring solution also comprises a colouring agent. The colouring agent comprises a mixture of at least two different metals or metal ions having a different atomic or ionic radius. Those metals or metal ions are present in certain amounts.

Rare earth element metals or ions include La, Ce, Pr, Nd, Sm, Eu, Gd, Tb, Dy, Ho, Er, Tm, Yb and Lu.

Transition metals or ions include metals of the groups IIIA, IVA, VA, VIA, VIIA, VIIIA, IB, IIB. Metals which were found to be especially useful for the purpose of the invention include Mn, Er and Pr.

The metals can be used either alone or in admixture with other metals, with the proviso that at least two different metals or ions are present.

In a certain embodiment of the invention, the colouring agent comprises at least about two different types of rare earth element metals or ions and at least one type of transition metal or ion. In a specific embodiment, the colouring agent comprises Pr, Er and Mn.

The rare earth element metals or ions have an atomic or ionic radius larger than the atomic or ionic radius of the transition metals or ions. Typically the ionic radius of the rare earth element metal ions is above about 0.9 Å, whereas the ionic radius of the transition metals ions is below about 0.9 Å or below about 0.8 Å. The size of the ionic radius usually depends on the charge of the ions and the coordination number. The above mentioned radii refer to a coordination number of 6 (effective ionic radii are reported e.g. in CRC Handbook of Chemistry and Physics, 76th edition, 1995-1996 CRC Press, Boca Raton, 12-14-12-15).

The amount of metal ions contained in the colouring solution should be sufficient to achieve an adequate colouring of the ceramic framework, especially after a firing process. The overall amount of colouring agent used is not particularly limited unless the result to be achieved cannot be obtained.

Good results can be achieved e.g. with an overall amount or colouring agent being present in the colouring solution in a range of about 0.01 to about 20 wt.-% of metal ions, or in the range of about 0.1 to about 17.0 wt.-%, or in the range of about 1 to about 15 wt.-% or in the range of about 2 to about 13 wt.-% or in a range of about 2 to about 12 wt.-% with respect to the weight of the whole composition.

The rare earth element metals or ions are present in the colouring solution in an amount of at least about 0.05 mol/l solvent or at least about 0.06 mol/l solvent at least about 0.07 mol/l or at least about 0.08 mol/l or at least about 0.1 mol/l or at least about 0.2 mol/l solvent.

There is no specific upper limit for the rare earth element metals or ions being present in the colouring solution. Preferably, the amount should be such that a storage stable solution can be obtained. Typically, the upper amount does not exceed a value of about 1 mol/l solvent or about 0.8 mol/l solvent or about 0.7 mol/l solvent or about 0.6 mol/l solvent.

The transition metals or ions are present in the solution in an amount of about 0.00001 to about 0.05 mol/l solvent or in an amount of about 0.0001 to about 0.03 mol/l solvent or in an amount of about 0.0005 to about 0.02 mol/l solvent or in an amount of about 0.0008 to about 0.01 mol/l solvent.

Usually, the colouring agent comprises salts comprising cations and anions. Anions which were found to be useful include $Cl^-$ (Y=1), $OAc^-$ (Y=1), $NO_3^-$ (Y=1), $NO_2^-$ (Y=1)$^-$, $CO_3^{2-}$ (Y=1), $HCO_3^-$ (Y=1), $ONC^-$ (Y=1), $SCN^-$ (Y=1), $SO_4^{2-}$ (Y=1)$^-$, $SO_3^{2-}$ (Y=1), gluturate (Y=2), lactate (Y=1), gluconate (Y=1), propionate (Y=1), butyrate (Y=1), glucuronate (Y=1), benzoate (Y=1), phenolate (Y=1), wherein Y indicates the number of complexing ligands being present in the anion.

Some of the ions mentioned above have more than 1 or 2 complexing ligands within the meaning of the invention. However, other anions might also be used containing more than 2 complexing ligands within the meaning of the invention, such as citrate (Y=3). Thus, the anion can fulfill two functions. First, it can act simply as a counter ion to the metal ion being present in the colouring agent, second, it can act as complexing agent.

Specific examples of colouring agents which can be used for the inventive colouring solution include acetates, carbonates and chlorides of Er, Mn and Pr.

In certain embodiments the inventive colouring solution might also comprise a complexing agent. If a complexing agent is present, it is typically present in the solution in an amount sufficient to dissolve the colouring agent in the solvent or to prevent precipitation of the colouring agent. The complexing agent can be present in an amount of at least about 2 wt.-% or at least about 5 wt.-% or at least about 15 wt.-% with respect to the amount of the whole composition. There is no upper limit, however, usually the amount of complexing agent used does not exceed an amount of about 60 wt.-% or about 50 wt.-% or about 40 wt.-% with respect to the amount of the whole composition.

E.g., the complexing agent can be used in a stoichiometric ratio with respect to the molar amount of the ions contained in the colouring agent.

Good results can be achieved, if the ratio of molar amount of complexing agent to the molar amount of metal ion being present in the colouring agent is equal to or greater than about 1 or about 2 or about 3.

If a complexing agent is added, it is usually added as a separate component of the composition. However, it can also be added as part of the colouring agent, e.g. as counter ion to the metal ion being present in the colouring component. Examples include citrate and ascorbate.

Without wishing to be bound by any theory, it is assumed that the complexing agent is able to form a complex with the metal ion(s) of the colouring agent assisting the colouring agent in dissolving in the chosen solvent and preventing the colouring agent from precipitating from the solution especially during storage, thus helping to obtain a better storage stable composition.

The complexing agent possibly forming a complex with the metal of the colouring agent can have different structures. The geometry usually depends on the "coordination number", the number of ligands attached to the metal. Usually one can count the ligands attached but sometimes even the counting can become ambiguous. Coordination numbers are normally between two and twelve, but large numbers of ligands are not uncommon. The number of bonds depends on the size, charge, and electron configuration of the metal ion. Most metal ions may have more than one coordination number.

Different ligand structural arrangements result from the coordination number. Most structures follow the points-on-a-sphere pattern (or, as if the central atom were in the middle of a polyhedron where the corners of that shape are the locations of the ligands), where orbital overlap (between ligand and metal orbitals) and ligand-ligand repulsions tend to lead to certain regular geometries.

The most observed geometries are listed below, but there are many cases which deviate from a regular geometry, e.g. due to the use of ligands of different types (which results in irregular bond lengths; the coordination atoms do not follow a points-on-a-sphere pattern), due to the size of ligands, or due to electronic effects:
 Linear for two-coordination,
 Trigonal planar for three-coordination,
 Tetrahedral or square planar for four-coordination
 Trigonal bipyramidal or square pyramidal for five-coordination,
 Octahedral (orthogonal) or trigonal prismatic for six-coordination,
 Pentagonal bipyramidal for seven-coordination,
 Square antiprismatic for eight-coordination, and
 Tri-capped trigonal prismatic (Triaugmented triangular prism) for nine coordination.

The increased stability of a chelated complex is called the chelate effect. In this respect, the complexing agent can also be characterized as a chelating agent (or a polydentate ligand), which can bond to more than one coordination site on the central atom. Because it is necessary to break all of the bonds to the central atom for the ligand to be completely displaced, it requires more energy to increase the number of separate molecules. If a chelate were replaced by several monodentate ligands (such as water or ammonia), the total number of molecules would decrease, whereas if several monodentate ligands were replaced by a chelate, the number of free molecules increases. The effect is therefore entropic in that more sites are used by less ligands and this leaves more unbonded molecules: a total increase in the number of molecules in solution and a corresponding increase in entropy.

It was found that good results can be achieved using complexing agents having at least 2, 3, 4, 5 or 6 coordinating ligands.

A coordinating ligand within the meaning of the invention is defined as a position within a molecular structure being able to interact with a metal ion. This interaction often leads to the formation of a complex structure as outlined above.

According to the present invention the complexing agents can be classified as follows:
 Complexing agents with 6 coordinating ligands (Y=6) include EDTA (ethylene diamine tetra acetic acid); 18-crown-6; 2,2,2-crypatand; polymeric ligands like poly acrylate, poly asparagate, acidic peptides with an "infinite" number of coordinating ligands are counted as complexing agents with 6 coordinating ligands.
 Complexing agents with 5 coordinating ligands (Y=5) include 15-crown-5; cyclo-pentadien.
 Complexing agents with 4 coordinating ligands (Y=4) include NTA (nitrilotriacetate); 12-crown-4; triethylentetramine; porphin$^{2-}$; phthalocyanin$^{2-}$ bis(salicilate) ethylenbis(imin)salen$^{2-}$.
 Complexing agents with 3 coordinating ligands (Y=3) include $C_3H_5O(COO)_3^{3-}$.
 Complexing agents with 2 coordinating ligands (Y=2) include $HC_6H_5O_7^{2-}$; salicylate, glycinate; lactate; acetylacetonate; propylendiamine; ascorbate $C_6H_6O_6^{2-}$; $C_3H_5O(COOH)(COO)_2^{2-}$.

A citrate is an ionic form of citric acid, such as $C_3H_5O(COO)_3^{3-}$, that is, citric acid minus three hydrogen ions. Citrates are compounds containing this group, either ionic compounds, the salts, or analogous covalent compounds, esters. Since citric acid is a tribasic acid, intermediate ions exist, hydrogen citrate ion, $HC_6H_5O_7^{2-}$ and dihydrogen citrate ion, $H_2C_6H_5O_7^-$. These may form salts as well, called acid salts. Salts of the hydrogen citrate ions are weakly acidic, while salts of the citrate ion itself (with an inert cation such as sodium ion) are weakly basic.

In general, in aqueous systems complexing agents having anionic groups as complexing ligands might be preferred. At least parts of the complexing ligands should be anionic. Complexing agents having only uncharged complexing ligands (or even cationic ligands) like pure amines (e.g. ethylendiamin at pH values at 8 to 14) might yield not sufficiently stable solutions.

If a complexing agent is present, it is typically present in an amount sufficient to dissolve the colouring agent in the solvent. A useful amount might fulfill the equation: X1/X2*Y greater than or equal to about 5, about 6 or about 7, with X1 being the amount of the complexing agent in [mol], X2 being the amount of the metal ions being present the colouring agent in [mol] and Y being the number of coordinating ligands of the complexing agent used.

As the colouring solution contains at least two different metals as part of the colouring agent, the individual amounts of metal ions present have to be added up. E.g., if the colouring solution contains 1 mol $MnCl_2$ and 2 mol $ErAc_3$, then X2 is 3.

If the colouring solution contains a certain amount of a specific complexing agent and a colouring agent, wherein the counter ion to the metal ion being present in the colouring agent can act as a complexing agent (such as citrate), then the amounts of complexing agent and the anion of the colouring agent have to be added up, too. E.g., if 1 mol of EDTA is used together with 1 mol iron citrate, then X1 is 2.

The inventive colouring solution can also comprise additives like stabilizers (including methoxy phenol hydrochinone or Topanol A), temporary binders, buffers (including acetate or amino buffers) or thixotropic substances (including polysaccharides, poly vinyl alcohols, polyethylenglycols (PEG), cellulose derivatives).

There is no need that any of these additives is present, however, they can be present. If they are present (that is, the amount of additive is greater than about 0.01 wt.-%), they are usually present in an amount up to about 4 wt.-% or up to about 6 wt.-% or up to about 12 wt.-% with respect to the weight of the whole composition.

In a very specific embodiment, an inventive colouring solution comprises an organic erbium salt (e.g. erbium acetate), an organic praseodymium salt (e.g. praseodymium acetate), minor traces of an organic manganese salt (e.g. manganese(II)acetate), a complexing agent (e.g. EDTA) and a solvent (e.g. water).

The pH-value of the colouring solution comprising water as a solvent is not particularly limited. Examples of useful pH-values are equal or greater than 1 or 2 or 3 or 4 or 5 or 6 or 7 or 8 or 9. Thus, the pH-value can be in a range of about 1 to about 9 or in the range of about 2 to about 8. Measurement of the pH-value can be achieved by means known by the person skilled in art. E.g. an instrument like Metrohm™ 826 or pH mobile indicator paper can be used.

In a preferred embodiment the coloring solution is transparent. A solution can be characterized as transparent within the meaning of the invention if a beam of visible light (about 400 nm to about 700 nm) is not scattered by the solution and cannot be observed by side view (no Tyndall effect). However, the intensity of the penetrating beam of visible light in direction of the beam may be weakened due to absorption of the light by the colouring metal ions.

The colouring solution should also have an adequate viscosity so that sufficient wetting of and penetration into the pores of the dental ceramic framework can be achieved. Good results can be obtained with a solution having a dynamic viscosity of about 1.0 mPa*s up to about 100 mPa*s or up to about 80 mPa*s or up to about 60 mPa*s.

The dynamic viscosity can be determined with an Physica MCR301 instrument using a cone plate geometry, diameter 50 mm, angle (cone) 1°, at 23° C. A typical shear rate is 200 rounds/s, however, generally the viscosity of liquids is independent from the shear rate in a wide range.

If the viscosity of the colouring solution is too high, the colour value of the coloured dental ceramic framework might be too bright. If the viscosity of the colouring solution is too low, the colour value of the coloured dental ceramic framework might be not homogenous.

According to one embodiment, the inventive colouring solution can comprise
   a solvent in an amount of about 60 to about 96 or in an amount of about 70 to about 94 or in an amount of about 80 to about 90 wt.-%,
   a colouring agent comprising rare earth element metals and transition metals in an amount of about 0.1 to about 20 or in an amount of about 0.5 to about 10 or in an amount of about 0.9 to about 5.0 wt.-%,
   a complexing agent in an amount of about 0 to about 60 or in an amount of about 5 to about 50 or in an amount of about 15 to about 40 wt.-%, and
   optionally additives (like e.g. stabilizers, temporary binders, buffers and/or thixotropic substances) in an amount of about 0.1 to about 12 or in an amount of about 1 to about 6 or in an amount of about 2 to about 4 wt.-%, wt.-% with respect to the weight of the whole composition (including the solvent(s)).

The invention also relates to a process of colouring dental ceramic articles with the colouring solution, the process comprising the steps of
   providing a colouring solution as described in the text of the invention and a preferably presintered dental ceramic article,
   treating the preferably presintered dental ceramic article with the colouring solution,
   optionally drying the treated dental ceramic article, and
   optionally firing or sintering the treated dental ceramic article, preferably to full density.

In a further embodiment, the dental article (e.g. framework) is coloured so as to match a predetermined or desired tooth color, e.g. a Vita™ shade from a shade guide, etc. In this respect the process described in the invention may optionally also include a step of selecting a suitable colouring solution out of a set of different colouring solutions based on colour, the tooth or teeth of the patient to be treated has. This selection step usually is made ahead of the treating step.

Thus, the inventive colouring solution may be part of a kit containing a couple of different colouring solutions, each of which is aligned to a specific tooth colour.

The firing or sintering step should be accomplished under conditions which results in a dental ceramic article having an acceptable tooth like colour (e.g. a colour which fits into the Vita™ shade guide.

Colouring the dental ceramic article is usually achieved by dipping the article into the solution. However, the solution can also be applied to the article by spraying, brushing, painting or by using a sponge or fabric.

The dental ceramic article is usually treated with the solution for about 1 to about 5 minutes, preferably from about 2 to about 3 minutes at room temperature (about 23° C.).

Preferably no pressure is used.

A penetration depth of the colouring solution into the dental ceramic article of about 5 mm is considered to be sufficient. The penetration depth can be determined as follows:

A plastic mesh (mesh size 500 μm) is located in a flat cup, which is filled with a colouring solution containing in addition a certain amount of an organic colourant (e.g. 100 ppm of Rhodamin B). A test bar of a presintered dental ceramic framework (LAVA™ Frame; 3M ESPE) having a size of Ø=about 24 mm, height=30 mm is placed on the plastic mesh and is soaked with the colouring solution for 2 min; dipping depth: 5 mm. The dental ceramic framework is taken out of the solution and is cutted into slices. The cutting edges are finished and the penetration of the solution into the dental ceramic framework is analysed with a fluorescence microscope. If the added organic colourant can be detected over the whole range of the dipping depth and not only in a small border area (about 2 mm), the penetration behaviour of the solution is considered to meet the practitioner's needs.

Drying the coloured dental ceramic article is not absolute necessary, but can be preferred to reduce the time needed for firing and to avoid undesired inhomogenous colour effects. Drying can be effected by simply storing the dental ceramic article on a surface at ambient conditions for a couple of hours (about 1 to about 3 hours).

The firing conditions are dependant on the ceramic material used. A furnace which can be used is the commercially available LAVA™ Therm (3M ESPE). During the firing process the coloured dental ceramic framework is sintered to its final shape, thereby undergoing changes with regard to dimension, density, hardness, raw breaking resistance and/or grain size.

The firing usually takes place for a $ZrO_2$ based ceramic at a temperature above about 1300° C., preferably above about 1400° C., more preferably above about 1450° C. and lasts for at least about 0.5 h, preferably for at least about 1 h, more preferably for at least about 2 h.

For an $Al_2O_3$ based ceramic the firing usually takes place at a temperature above about 1350° C., preferably above about 1450° C., more preferably above about 1650° C. and lasts for at least about 0.5 h, preferably for at least about 1 h, more preferably for at least about 2 h.

Generally, the sintering or firing conditions are adjusted such that the sintered dental ceramic article has a density of equal or greater than about 98% compared with the theoretically achievable density. In one embodiment this can be accomplished using a temperature above about 1300° C.

The present invention also relates to dental ceramic articles (preferably presintered dental ceramic framework) treated with the inventive colouring solution and dental ceramic articles obtainable after such a treatment step and a sintering step.

Dental ceramic articles shaded with liquids according to the present invention show typically a "warm", tooth like color, unlike e.g. solutions of pure Praseodymium acetate.

The dental ceramic article after such a sintering step usually shows at least one or more of the following features:
  Weibull strength (sigma 0): at least about 800 MPa, or at least about 900 MPa or at least about 1000 MPa,
  L*a*b value:
    L* in the range of about 65 to about 80 or in the range or about 67 to about 78,
    a* in the range of about −1.5 to about 4 or in the range or about −1.1 to about 3.5,
    b* in the range or about 5 to about 32 or in the range or about 7 to about 28,
  measured as described in the text of the invention.

A more detailed description of the measurement of the L*a*b* values is given in the example section below.

The Weibull strength (sigma 0) of the sintered dental ceramic article can be determined according to the "punch on three ball test" (biaxial flexural strength) described in DIN EN ISO 6872, edition March 1999, with the following modifications: diameter of steel ball: 6 mm; diameter of support circle: 14 mm; diameter of flat punch: 3.6 mm; diameter of sample disc: 19-20 mm, thickness of sample disc: 1.6 mm (+/−0.1 mm); no grinding and polishing of samples.

Typically, the b value is below about 32 or below about 28, whereas the values for L and a can be chosen freely.

The colouring solution of the invention does not necessarily comprise any organic colorants or colouring means that will only tint the surface but not the bulk, like pigments.

It is not mandatory, but if possible, the colouring solution should not or only contain a small amount of ingredients which can be detrimental to the firing equipment during the sintering process, like halogen (fluorine, chlorine, bromine or iodine). In this respect in certain embodiment of the present invention, the amount of halogen ions contained in the colouring solution should be kept low, e.g. below about 0.3 mol/l or below about 0.2 mol/l or below about 0.15 mol/l.

Moreover, in another embodiment of the invention, the colouring solution is essentially free of iron or iron ions.

Thus, the content of iron or iron ions is usually below about 0.001 mol/l or below about 0.0001 or even below about 0.00001 mol/l solvent.

The inventive colouring solution can be applied to presintered ceramic bodies of various compositions, especially such comprising or preferably consisting essentially of $ZrO_2$ and/or $Al_2O_3$, respectively. These compositions are known to the skilled person in the art (examples of useful compositions are described e.g. in U.S. Pat. No. 6,709,694; the content of which is herewith incorporated by reference). The $ZrO_2$ is preferably stabilized with $Y_2O_3$. Other presintered ceramic articles which can be used are include those described e.g. in US 2004/0119180 or U.S. Pat. No. 6,713,421, the content of both of which is herewith incorporated by reference.

Thus, the invention also relates to a process of using a colouring solution comprising a solvent and a colouring agent comprising rare earth element metals or ions and mixtures thereof as described in the present text for reducing the sintering distortion of dental ceramic articles during or after a sintering or firing step The invention is hereinafter described by examples, the content of which is not intended to limit the scope of the invention.

EXAMPLES

Measurements
pH-Value
The pH-value was determined using a mobile pH-indicator paper available from Merck KGaA, Darmstadt Germany (pH 0-14, pH indicator strips, non bleeding, Art. Nr. 1.09535.0001)
L*a*b* Values
The L*a*b* values were determined using a commercially available Hunter Lab System (Hunter Lab., Corp.) according to the instructions of use given in the manufacturer's operation manual referring to the formulas given in DIN 6174 (Section 2). The values were determined using dense sintered specimens (diameter: 12-20 mm, thickness: 1.5 mm). The surface of the specimens was scratch free polished (grinding steps; 74 µm, 10 µm, 9 µm, 3 µm). The following adjustments were made at the Hunter Lab: measuring orifice: 6 mm, measuring spot size: 6 mm.

Further hints to the measuring of L*a*b* values can also be found in U.S. Pat. No. 6,756,421 column 4, lines 26 to 55, which is herewith incorporated by reference.

"L*" refers to the brightness (100=white, 0=black), "a*" refers to the red-green axis and "b*" refers to the yellow-blue axis.

Sintering Distortion—Colouring of Test Bars and Model Experiment to Show Influence on Distortion During a Sintering Step:

Bars of commercially available pre-sintered LAVA™ Frame Zirconia material with a size of 41.0×4.0×3.0 mm were prepared by using a commercial available LAVA™ milling unit. 2 grooves perpendicular to the long axis of the bar were prepared on the 4 mm side of the bar in a distance of 30 mm of each other. Since the grooves were placed symmetrically with respect to the long axis of the bar, the distance of each groove to the end of the bar was 5.5 mm (in direction long axis). The grooves were prepared with a tool holder for grinding wheels using a Soflex™ disk of 0.5 mm thickness and approx. 15 mm diameter of the grinding wheel. The respective groove had approx 0.4 mm width and 0.1 mm depth. Dust was removed of the surface by applying a compressed air stream. The bars were then submerged in the respective colouring solution for about 120 s. Excessive liquid on the surface of the bars was removed gently with humid pulp.

The prepared bars were placed on platinum wire sinter appliances (swing form, 3M ESPE item number 78990244697, diameter of "swing" wire 0.32 mm, supporting wire 0.65 mm, height of whole appliance approx. 35 mm) so that the wires were fixed within the above mentioned grooves. The sinter appliances themselves were placed in a "honeycomb" sinter support carrier of mullite to ensure sufficient mechanical stability during sintering (diameter of hollow combs approx. 1.85 mm, height approx. 11.5 mm). Sinter support carries are commercially available (e.g. 3M ESPE; item number 78990243988). Whereas the lower part of the sintering appliance is more or less fixed and only slightly movable in the support carrier, the upper part is freely movable like a swing as described in WO 2006/108677 A1, FIG. 4. The honeycomb body was placed in a bowl of alumina. The resulting height of the bar over the honeycomb alumina sinter support was approx. 10 mm) The bars were then subjected to typical sintering process used for 3M ESPE LAVA™ zirconia dental material (3.5 h drying at room temperature, heating up to 1500° C. with a heating rate of 10° C./min, holding at 1500° C. for 2 h and passive cooling to room temperature, overall cycle time approx. 11 h). The obtained zirconia materials were fully dense and corresponded to the typical 3M ESPE LAVA™ material.

to measuring bar. By using the SKEW function of the microscope (SKEW: a function offered by the measuring microscope facilitating the measuring process) a zero line between the edges of the distorted test bar was drawn. Subsequently by shifting the xy-board of the microscope the point of maximal displacement was adjusted to the zero line. By reading the values of the xy-board before and after shifting the values for the maximum displacement were calculated.

The measured values are given in Table 1 below.

Preparation of the Colouring Solutions

General Description

The respective salts of rare earth element metals or transition metals were dissolved in a suitable solvent under stirring at 23° C. If desired and appropriate, certain amounts of complexing agent and/or other additives were added.

The water used was de-ionized water. Complexing and colouring agents used are commercially available at Sigma Aldrich Co. or ABCR GmbH & CO. KG (Karlsruhe, Germany).

Solutions Nos. 2 to 6 were prepared according the general description given above. The components and amounts used are given in Table 1 below. Colouring solution No. 1 is commercially available as FS4 LAVA™ Frame Shade dying Liquid (3M ESPE; item number 68577). Colouring solution No. 2 is a comparative example.

Solutions 1 to 6 were tested with respect of their capability for reducing sintering distortion, pH value and L*a*b values. The value given in brackets is the standard deviation.

TABLE 1

| | Complexing Agent [mol/l] | Colouring Agent [mol/l] | Colouring Agent [mol/l] | Colouring Agent [mol/l] | Solvent | pH-value | Distortion [mm] | Additive [w.-%] | L* | a* | b* |
|---|---|---|---|---|---|---|---|---|---|---|---|
| 1 | n.a. | FeCl₃ 0.124 | ErCl₃ 0.289 | n.a. | water | 1 | 0.090 (0.017) | PEG 350006 | 69.6 | 3.0 | 24.5 |
| 2 | n.a. | PrAc₃[1] 0.022 | n.a. | n.a. | water | 7 | 0.078 (0.009) | n.a. | 72.6 | 0.13 | 34.6 |
| 3 | EDTA[2] 0.438 | PrAc₃ 0.021 | ErAc₃ 0.421 | MnAc₂ 0.0006 | water | 4 | 0.0030 (0.011) | n.a. | 67.9 | 3.0 | 24.1 |
| 4 | n.a. | PrCl₃ 0.017 | ErCl₃ 0.433 | MnCl₂ 0.001 | water | 3 | 0.068 (0.007) | PEG 350007 | 71.5 | 3.50 | 21.7 |
| 5 | (NH₄)₂H-citrate 0.89 | PrAc₃ 0.021 | ErAc₃ 0.421 | MnCl₂ 0.001 | water | 5 | 0.015 (0.010) | n.a. | 67.9 | 3.60 | 25.2 |
| 6 | Citric Acid 0.758 | PrAc₃ 0.017 | ErAc₃ 0.35 | MnCl₂ 0.001 | water | 2 | 0.00 (0.00) | n.a. | 68 | 3.22 | 24.0 | n.a. means not applicable;
Ac = acetate
[1] 0.75 wt.-% solution of PrAc₃ in water.
[2] added as EDTA diammonium salt.

In FIG. 1 schematically shows how the sintering of the ceramic framework was accomplished. The sinter appliances (1) are placed in a support carrier (2) and the test bar (3) placed on the sinter appliances (1). The test bar (1) is slightly deformed after the sintering process. In the embodiment according to FIG. 1 four individual test bars are sintered simultaneously.

Figure 2:
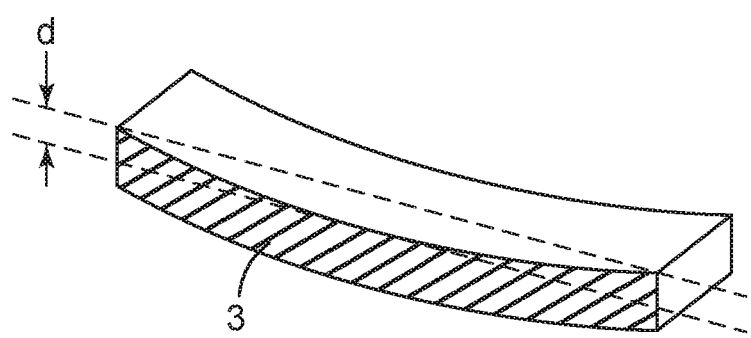
FIG. 2 graphically shows how the distortion of dental ceramic articles (e.g., frameworks) was determined.
Figure 3:
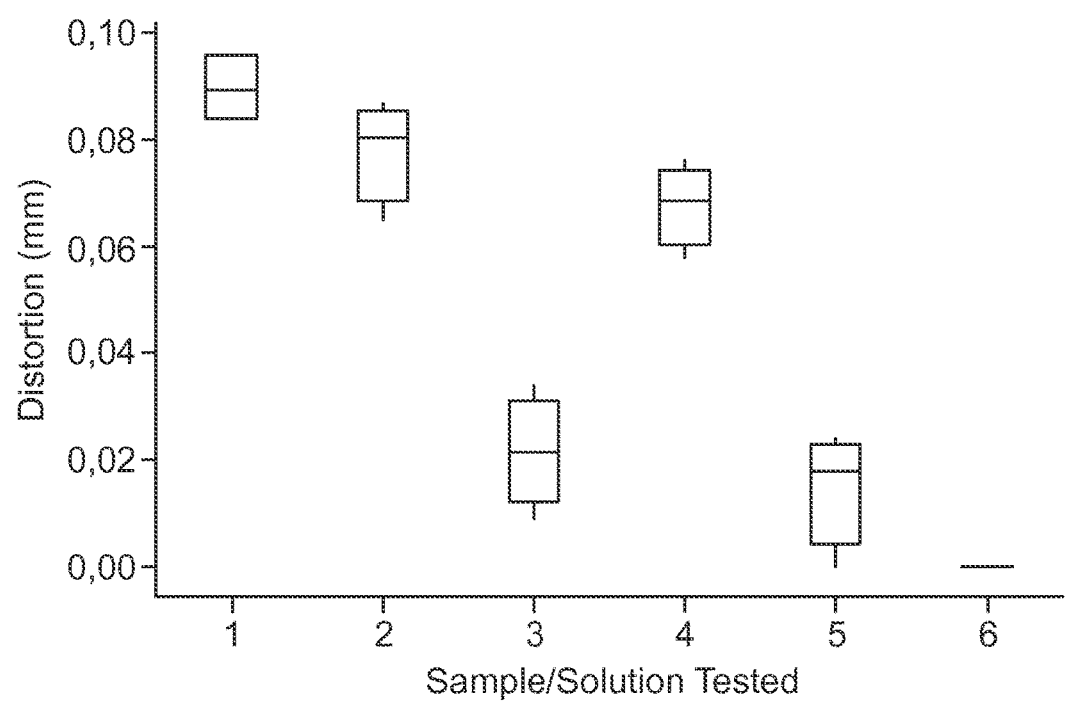
FIG. 3 shows a box plot of the measured values.

FIG. 2 graphically shows how the distortion was determined. The distortion was measured with a calibrated optical measuring microscope (Measuring Microscope Nikon MM-40). The respective distorted zirconia test bar (3) was closely applied to the measuring bar of the microscope. The test bar typically had contact to the measuring bar at its two ends (with respect to the long axis of the test bar). Then the microscope in the incident light mode was focused at the two edges of the test bar on the upper side that were in contact FIG. 3 graphically shows the results of Table 1 with regard to distortion as box plot. Four individual measurements were done for each colouring solution and the mean value determined. The line in the box represents the mean value. The size of the box indicates the standard deviation. The measured values (y-axis) are given in mm. The number of the colouring solution (x-axis) corresponds to the numbering given in Table 1 above.

The invention claimed is:

1. A colouring solution for colouring a dental ceramic article, the solution comprising:
   a solvent and
   a colouring agent, comprising
      a rare earth element metal or ion being present in the solution in an amount of at least about 0.05 mol/l solvent, and a transition metal or ion being different from the rare earth element metal or ion and being present in the solution in an amount of about 0.00001 to about 0.03 mol/l solvent; wherein the solution is transparent to visible light.

2. The colouring solution according to claim 1, wherein the colouring agent further comprises at least one anion selected from the group consisting of $Cl^-$, $OAc^-$, $NO_3^-$, $NO_2^-$, $CO_3^{2-}$, $HCO_3^-$, $ONC^-$, $SCN^-$, $SO_4^{2-}$, $SO_3^{2-}$, gluturate, lactate, gluconate, propionate, butyrate, glucuronate, benzoate and phenolate.

3. The colouring solution according to claim 1, wherein the rare earth element metal is selected from the group consisting of La, Ce, Pr, Nd, Sm, Eu, Gd, Tb, Dy, Ho, Er, Tm, Yb, Lu and mixtures thereof.

4. The colouring solution according to claim 1, wherein the transition metal is selected from the columns of the Periodic Table of Elements starting with the elements Sc, Ti, V, Cr, Mn, Fe, Co, Ni, Cu and Zn and the metals listed below those elements and mixtures thereof.

5. The colouring solution according to claim 1, wherein the solvent is selected from the group consisting of water, alcohols, dipolar aprotic liquids, apolar liquids, mixtures of water with alcohols, and mixtures of water and dipolar aprotic liquids.

6. The colouring solution according to claim 1 having at least one of the following features:

a dynamic viscosity below about 100 mPa*s at 23° C., or
for water containing solutions a pH-value in the range between about 1 to about 9.

7. The colouring solution according to claim 1 further comprising additives selected from the group consisting of stabilizers, temporary binders, buffers, thixotropic substances and mixtures thereof.

8. The colouring solution according to claim 1 further comprising a complexing agent present in an at least stoichiometric ratio with respect to the metal ion present in the colouring agent.

9. The colouring solution according to claim 8, wherein the complexing agent is selected from the group consisting of crown ethers, cryptands, ethylenediaminetriacetate and its salts, ethylenediaminetetraacetate (EDTA) and its salts, nitrilotriacetate (NTA) and its salts, citric acid and its salts, triethylentetramine, porphin and mixtures thereof.

10. The colouring solution according to claim 1, the colouring solution comprising the rare earth element metal or ion in an amount of about 0.05 to about 1 mol/l solvent,
a halogen ion in an amount below about 0.3 mol/l solvent, and
an additive in an amount of about 0 to about 15 wt.-% with respect to the total weight of the colouring solution.

11. A process of colouring a dental ceramic article comprising the steps of a) providing a colouring solution according to claim 1 and a dental ceramic article, and
b) treating the ceramic article with the colouring solution.

12. The process according to claim 11 further comprising sintering the treated ceramic article to obtain a final density.

13. A dental ceramic article obtained by the process of claim 11, wherein the dental ceramic article comprises $ZrO_2$, $Al_2O_3$, or combinations thereof and has the shape of a crown, inlay, onlay, abutment, bridge or implant.

14. A dental ceramic obtained by the process of claim 12, wherein the dental ceramic article has a Weibull strength (sigma 0) of at least about 800 MPa.

15. A process for reducing the sintering distortion of a dental ceramic article, the process comprising:

a) providing a colouring solution and a pre-sintered dental ceramic article,
b) treating the ceramic article with the colouring solution, and
c) sintering the ceramic article
wherein the colouring solution is transparent to visible light and comprises a solvent and a colouring agent, the colouring agent comprising a rare earth element metal or ion and mixtures thereof, the metal or ion being present in an amount of at least about 0.05 mol/l solvent; and a transition metal or ion being different from the rare earth element metal or ion and being present in the solution in an amount of about 0.00001 to about 0.03 mol/l solvent.

16. The process according to claim 11 further comprising drying the treated ceramic article.

17. The process according to claim 12, wherein the dental ceramic article has a density of equal or greater than about 98% compared to the theoretically achievable density when sintered.

18. The dental ceramic article obtained by the process of claim 12, wherein the dental ceramic article has a L* value in the range of about 65 to about 80, an a* value in the range of −1.5 to 4, and a b* value in the range or about 5 to about 32.

19. The colouring solution according to claim 1, wherein at least two different rare earth element metals or ions are present.

20. The colouring solution according to claim 19, wherein the two different rare earth element metals or ions are Er and Pr.

21. The colouring solution according to claim 1 further comprising a complexing agent in an amount from about 2 wt % to about 60 wt % with respect to the total weight of the colouring solution.

22. The colouring solution according to claim 1, wherein the transition metal or ion is present in the solution in an amount of about 0.0001 to about 0.03 mol/l solvent.

23. The colouring solution according to claim 1, wherein the rare earth element metal or ion is present in the solution in an amount of at least about 0.06 mol/l solvent.

24. The colouring solution according to claim 1, wherein the rare earth element metal or ion is present in the solution in an amount of at least about 0.06 mol/l solvent and the transition metal or ion is present in the solution in an amount of about 0.0005 to about 0.02 mol/l solvent.

* * * * *

UNITED STATES PATENT AND TRADEMARK OFFICE
CERTIFICATE OF CORRECTION

PATENT NO. : 10,065,895 B2
APPLICATION NO. : 12/669846
DATED : September 4, 2018
INVENTOR(S) : Ruediger Franke et al.

It is certified that error appears in the above-identified patent and that said Letters Patent is hereby corrected as shown below:

In the Specification

Column 6
Line 21, delete "Flurorite" and insert -- Fluorite --, therefor.

Column 9
Line 43, after "Coordination" insert -- , --.

Column 10
Line 12, delete "-crypatand;" and insert -- -cryptand; --, therefor.
Line 19-20, delete "triethylentetramine;" and insert -- triethylenetetramine; --, therefor.

Column 14
Line 21, after "step" insert -- . --.

In the Claims

Column 17
Line 44, in Claim 9, delete "triethylentetramine," and insert -- triethylenetetramine, --, therefor.

Signed and Sealed this
Twenty-seventh Day of November, 2018

Andrei Iancu
*Director of the United States Patent and Trademark Office*